United States Patent
Hatakeda et al.

(10) Patent No.: US 7,084,269 B2
(45) Date of Patent: Aug. 1, 2006

(54) PROCESS FOR PRODUCING LACTAM

(75) Inventors: Kiyotaka Hatakeda, Miyagi (JP); Osamu Sato, Miyagi (JP); Yutaka Ikushima, Miyagi (JP); Kazuo Torii, Miyagi (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/471,750

(22) PCT Filed: Mar. 5, 2002

(86) PCT No.: PCT/JP02/02029

§ 371 (c)(1),
(2), (4) Date: Sep. 25, 2003

(87) PCT Pub. No.: WO02/076942

PCT Pub. Date: Oct. 3, 2002

(65) Prior Publication Data

US 2004/0097727 A1    May 20, 2004

(30) Foreign Application Priority Data

Mar. 26, 2001  (JP) ............................. 2001-88085

(51) Int. Cl.
*C07D 201/04*    (2006.01)
(52) U.S. Cl. .................... 540/535; 540/536
(58) Field of Classification Search ............... 540/535, 540/536
See application file for complete search history.

(56) References Cited

FOREIGN PATENT DOCUMENTS

JP    10-287644    10/1998

OTHER PUBLICATIONS

J. Am. Chem. Soc., vol. 122, pp. 1908-1918 2000.
J. Org Chem., vol. 63, pp. 9100-9102 1998.

*Primary Examiner*—Bruck Kifle
(74) *Attorney, Agent, or Firm*—Oblon, Spivak, McClelland, Maier & Neustadt, P.C.

(57) ABSTRACT

It is an object of the present invention to provide an efficient method of continuously producing a lactam in high-temperature high-pressure water, and the present invention relates to a method of producing a lactam characterized by efficiently synthesizing the lactam while suppressing oxime hydrolysis by introducing an oxime as a reaction substrate and an acid into a reaction zone through which high-temperature high-pressure water is flowing, or introducing an oxime into flowing high-temperature high-pressure water containing an acid, thus raising the temperature of the reaction substrate to put the reaction substrate into a pre-scribed high-temperature high-pressure state within a short time and subjecting the reaction substrate to reaction; through the method, the lactam can be efficiently and continuously synthesized at a high rate from the oxime using an acid catalyst in water at a high temperature of at least 250° C. and a high pressure of at least 15 MPa.

13 Claims, 3 Drawing Sheets

Fig. 3 and more particularly to a novel continuous production method of continuously producing a lactam by carrying out a rearrangement reaction of an oxime in high-temperature high-pressure water using an acid. Yet more specifically, the present invention provides a method that is preferable and useful as an industrial technique, enabling production of a lactam without the need for treatment to neutralize a large amount of used waste sulfuric acid as seen in the case of a conventional production method in which fuming sulfuric acid is used as a catalyst.

PROCESS FOR PRODUCING LACTAM

BACKGROUND OF THE INVENTION

1. Field of the Invention

The present invention relates to a method of continuously producing a lactam from an oxime in high-temperature high-pressure water, and more particularly to a novel continuous production method of continuously producing a lactam by carrying out a rearrangement reaction of an oxime in high-temperature high-pressure water using an acid. Yet more specifically, the present invention provides a method that is preferable and useful as an industrial technique, enabling production of a lactam without the need for treatment to neutralize a large amount of used waste sulfuric acid as seen in the case of a conventional production method in which fuming sulfuric acid is used as a catalyst.

2. Description of the Related Art

Conventionally, a lactam such as ε-caprolactam, which is used as a raw material of nylon 6, is industrially produced by a Beckmann rearrangement from a carbonyl compound oxime such as cyclohexanone oxime. A highly concentrated acid catalyst such as fuming sulfuric acid is used in this rearrangement reaction, and because the reaction is carried out while boiling, hydrolysis of the oxime will be brought about by the presence of even a very small amount of water in the system, resulting in a drop in the yield of the lactam. To prevent this, the usual method is to carry out the reaction while boiling, using fuming sulfuric acid as the acid catalyst. With this method, because the reaction is carried out under harsh conditions using fuming sulfuric acid, there are known to be problems with regard to corrosion of the materials of the apparatus, the hazardousness of the production process, and processing of the byproduct ammonium sulfate. When recovering the lactam, the sulfuric acid used must be neutralized with ammonia, and more than 2 kg of ammonium sulfate is produced as a byproduct per 1 kg of the lactam. Ammonium sulfate has little commercial value, and hence using the ammonium sulfate has become difficult, and thus it has become necessary to process the ammonium sulfate.

In recent years, fears over deterioration of the global environment have heightened, and in the chemical industry there have been calls for the development of environmentally friendly chemical processes that are simple and efficient, according to which reaction can be completed within a short time, and according to which hazardous substances are not used. Regarding lactam production, there have been calls for the development of a novel production process that is efficient, and does not use fuming sulfuric acid, with which there are problems in terms of corrosion of the materials of the apparatus, operational safety, and the environment.

As methods for resolving the above problems, two methods have been proposed in which reaction is carried out in high-temperature high-pressure water and an acid catalyst such as fuming sulfuric acid is not used at all, namely (1) a batch type synthesis method (O. Sato, Y. Ikushima and T. Yokoyama, Journal of Organic Chemistry 1998, 63, 9100–9102), and (2) a flow type synthesis method (Y. Ikushima, K. Hatakeda, O. Sato, T. Yokoyama and M. Arai, Journal of the American Chemical Society 2000, 122, 1908–1918).

With the batch type synthesis method (1), cyclohexanone oxime is sealed in a stainless steel tube of internal volume 10 ml, the stainless steel tube is put into a salt bath to raise the temperature thereof to 200 to 400° C. within 20 to 30 seconds, and reaction is carried out for 3 minutes to obtain the product. It is considered that this method is not suitable as a mass production process, but nevertheless the method has attracted attention as a synthesis method that does not use a highly concentrated acid catalyst such as fuming sulfuric acid. Because the method is operated intermittently in order to bring the reaction to completion one batch at a time, a time of approximately 20 to 30 seconds is required to raise the temperature to the set reaction temperature. There is thus a drawback in that a large amount of the hydrolysis product cyclohexanone tends to be produced while the temperature is being raised, and hence the yield of the targeted ε-caprolactam is quite low. Moreover, cyclohexanone is a raw material of cyclohexanone oxime, and hence the reaction goes in the reverse direction, which is a fatal drawback for an industrial process.

With the flow type synthesis method (2), on the other hand, the method is operated continuously and hence it is considered that the method is suitable for mass production, but a cyclohexanone oxime aqueous solution at room temperature is heated to produce the high-temperature high-pressure carrier water, and hence one would imagine that raising the temperature up to the set reaction temperature must take a long time. Accordingly, in an experiment in which reaction was carried out for 113 seconds under conditions of 350° C. and 22.1 MPa, the result was that only cyclohexanone was obtained as a product, with ε-caprolactam not being produced at all. Moreover, it is reported that even at 374.5° C., ε-caprolactam and cyclohexanone are both produced. Consequently, it seems that with this method, as with the batch type synthesis method (1), raising the temperature takes time, and hence a large amount of cyclohexanone is produced through hydrolysis of the cyclohexanone oxime while the temperature of the solvent water is passing from, for example, 100 to 300° C., and thus there is a drawback in that the yield of the targeted ε-caprolactam is reduced.

SUMMARY OF THE INVENTION

Amid the situation described above and in view of the prior art described above, the present inventors carried out various studies into a method of producing a lactam from an oxime in high-temperature high-pressure water, and through this process discovered that to continuously and efficiently produce a lactam from an oxime in high-temperature high-pressure water, it is important to raise the temperature of the oxime to the set reaction temperature within a short time in the presence of an acid; the present inventors then carried out further studies based on this finding, thus accomplishing the present invention.

That is, the present invention was accomplished with an object of providing a method of efficiently producing a lactam while inhibiting production of cyclohexanone, by introducing an oxime as a substrate and an acid into high-temperature high-pressure water, or introducing an oxime into high-temperature high-pressure water containing an acid, thus carrying out reaction with the time taken to raise the temperature of the substrate shortened.

The synthesis method of the present invention, which was developed by the present inventors through various experiments, is, for example, a method of producing caprolactam more efficiently and in a shorter time than with a conventional method, comprising continuously introducing an oxime aqueous solution or an oxime and an acid directly into a reaction zone in which there is high-temperature high-pressure water, whereby a set reaction temperature is reached within a short time, and hence a rearrangement reaction of the oxime is promoted by the acid with hydrolysis of the oxime being suppressed.

To resolve the problems described above, the present invention is constituted from the following technical means.

(1) A method of producing a lactam, wherein an oxime as a reaction substrate and an acid are introduced into a reaction zone in which there is high-temperature high-pressure water, thus raising the temperature of the oxime to put the oxime into a prescribed high-temperature high-pressure state within a short time and subjecting the oxime to reaction, whereby the lactam is synthesized while suppressing hydrolysis of the oxime.

(2) The method of producing a lactam according to (1) above, wherein a substrate aqueous solution having the oxime and the acid dissolved therein is introduced into the continuously flowing high-temperature high-pressure water, thus subjecting the oxime to the reaction in the prescribed high-temperature high-pressure state.

(3) The method of producing a lactam according to (1) above, wherein the oxime and the acid are introduced separately into the continuously flowing high-temperature high-pressure water, thus subjecting the oxime to the reaction in the prescribed high-temperature high-pressure state.

(4) A method of producing a lactam, wherein an oxime is introduced into high-temperature high-pressure water containing an acid, thus raising the temperature of the oxime to put the oxime into a prescribed high-temperature high-pressure state within a short time and subjecting the oxime to reaction.

(5) The method of producing a lactam according to (4) above, wherein the oxime, or a substrate aqueous solution having the oxime dissolved therein, is introduced into the continuously flowing high-temperature high-pressure water containing the acid, thus subjecting the oxime to the reaction in the prescribed high-temperature high-pressure state.

(6) The method of producing a lactam according to any of (1) through (5) above, wherein the oxime is introduced in a molten state, thus subjecting the oxime to the reaction in the prescribed high-temperature high-pressure state.

(7) The method of producing a lactam according to any of (1) through (6) above, wherein the oxime is subjected to the reaction in the high-temperature high-pressure water at a temperature of at least 250° C. and a pressure of at least 15 MPa.

(8) The method of producing a lactam according to any of (1) through (7) above, wherein the temperature of the oxime is raised to put the oxime into the prescribed high-temperature high-pressure state within a short time of not more than 3 seconds and the oxime is subjected to the reaction.

(9) The method of producing a lactam according to any of (1) through (8) above, wherein the oxime is subjected to the reaction in the prescribed high-temperature high-pressure state for a time of not more than 60 seconds.

(10) The method of producing a lactam according to any of (1) through (5) above, wherein at least one selected from the group consisting of sulfuric acid, hydrochloric acid, nitric acid and acetic acid is used as the acid.

(11) The method of producing a lactam according to any of (1) through (9) above, wherein cyclohexanone oxime is used as the oxime.

Following is a more detailed description of the present invention.

To facilitate explanation of the present invention, a detailed description will be given taking as an example the case of producing a lactam by introducing an aqueous solution containing an oxime and an acid into high-temperature high-pressure water, whereby a reaction temperature of 250 to 400° C. is reached within a short time of, for example, not more than 3 seconds, and reaction takes place under a reaction pressure of 15 to 40 MPa.

The production method of the present invention, which was developed by the present inventors through various experiments, is, for example, a method in which an aqueous solution containing cyclohexanone oxime and an acid is continuously introduced into a reaction zone through which high-temperature high-pressure water is flowing, whereby the temperature is made to reach a set reaction temperature within a short time of not more than 3 seconds, and hence ε-caprolactam is synthesized through a rearrangement reaction of the cyclohexanone oxime, while suppressing hydrolysis. The production method of the present invention is a method of efficiently producing a lactam from an oxime using high-temperature high-pressure water as the reaction zone or reaction solvent, and using an acid as a catalyst; an organic solvent is not needed in the reaction. Moreover, there is no need to neutralize the used acid when subjecting the lactam such as ε-caprolactam to separation and purification. Consequently, according to the present method, waste matter that must be processed such as waste solvent and/or ammonium sulfate is hardly discharged. Moreover, only a very small amount of cyclohexanone is produced through hydrolysis of the cyclohexanone oxime. Unreacted raw material, and the acid or aqueous solution can be reused in the reaction of the present invention. Furthermore, with the method of the present invention, the product can be produced efficiently, continuously, and at a high rate, and hence the method of the present invention is considered to be the best means of producing lactams.

Following is a description of the method of producing a lactam of the present invention.

In the present invention, for example, an oxime aqueous solution or an oxime is continuously introduced, together with or separately to an acid, into a reaction zone in which there is high-temperature high-pressure water, whereby the temperature is made to reach a set reaction temperature within a short time, and hence a lactam can be produced in the presence of the acid efficiently with a shorter reaction time than with a conventional method, and selectively with hydrolysis of the oxime being suppressed. The reaction will proceed in high-temperature high-pressure water even if acid is not introduced at all, but the reaction yield is often low; with the present invention, by making an acid be involved in the reaction, the reaction efficiency can be improved, and hence the method of the present invention is superior as a method for efficiently producing a lactam.

An oxime used as the substrate raw material in the present invention is represented by undermentioned general formula (1), wherein n is an integer from 1 to 9, and $R_1$ is hydrogen or an alkyl group. As an alkyl group, any having 1 to 20 carbon atoms can be used, for example a methyl group, an ethyl group, a propyl group or a butyl group. An example of the oxime is cyclohexanone oxime, but the present invention is not limited to this.

(1)

A lactam obtained in the present invention is represented by undermentioned general formula (2), wherein n is an integer from 1 to 9, and $R_1$ is hydrogen or an alkyl group. As an alkyl group, any having 1 to 20 carbon atoms can be used, for example a methyl group, an ethyl group, a propyl group or a butyl group.

(2)

The lactam obtained in the present invention is a many-membered ring lactam having at least five members in the ring, for example a 5-membered ring lactam, a 6-membered ring lactam or a 7-membered ring lactam. Examples include ε-caprolactam, γ-butyrolactam, γ-valerolactam and δ-valerolactam, but the present invention is not limited to these.

As a specific example of the production of a lactam according to the present invention, that is an example in which a 7-membered ring lactam is produced, undermentioned general formula (3) shows the reaction formula for synthesizing ε-caprolactam from cyclohexanone oxime.

(3)

It is known that the synthesis of a lactam through a Beckmann rearrangement of an oxime proceeds in the presence of a fuming sulfuric acid catalyst. The fact that a lactam can be produced efficiently through a Beckmann rearrangement of an oxime by using a low-concentration acid in a high-temperature high-pressure aqueous reaction as in the present invention is interesting. It is conjectured that in high-temperature high-pressure water it may be that an acid catalyst function appears through production of protons, polarization of the water molecule structure, or the like, and hence a lactam is produced through Beckmann rearrangement of the oxime. Furthermore, it is an extremely interesting result that the Beckmann rearrangement of the oxime proceeds more efficiently upon adding a low-concentration acid as in the present invention. Further verification through physicochemical studies into high-temperature high-pressure water in the future is hoped for.

According to the present invention, the oxime that is the substrate can be put into a prescribed high-temperature high-pressure state within a short time, and hence hydrolysis of the oxime can be suppressed, and moreover by making an acid be present in the reaction zone, the lactam can be produced efficiently. Note, however, that a small amount of an amino acid may also be produced through the present reaction. For example, in the case of synthesizing ε-caprolactam from cyclohexanone oxime by reacting for 0.728 seconds under a high temperature of 375° C. and high pressure of 40 MPa, in the case that hydrochloric acid was made to be present at a concentration of 1.4 mol % relative to the reaction substrate, an ε-caprolactam yield of 96.2% and a 6-aminocaproic acid yield of 3.5% were obtained. In the case that such an acid was not present, the ε-caprolactam yield was 41.4% and the 6-aminocaproic acid yield was 0.3%. Conversion of 6-aminocaproic acid into ε-caprolactam is relatively easy, and this reaction also proceeds readily in high-temperature high-pressure water. In the above two reactions, only a very small amount of the hydrolysis product cyclohexanone was detected.

As the water used as the raw material of the high-temperature high-pressure water in the present invention, distilled water, ion exchange water, tap water, ground water and so on can be preferably used. When using such a water as the raw material of the high-temperature high-pressure water, in particular in the case of using the high-temperature high-pressure water in a supercritical state, dissolved oxygen may cause oxidative decomposition of organic matter, and hence it is preferable to use the water after removing the dissolved oxygen in advance by bubbling with nitrogen gas or the like. In the case of using the high-temperature high-pressure water in a subcritical state, there is no particular need to remove dissolved oxygen from the raw material water, although this may be done.

Regarding the acid used as a catalyst in the present invention, either a mineral acid or an organic acid can be used. A mineral acid such as sulfuric acid, hydrochloric acid, nitric acid, perchloric acid or carbonic acid can be preferably used. Alternatively, an organic acid such as acetic acid, oxalic acid, lactic acid or tartaric acid can be preferably used. One of these acids can be used as the catalyst, or two or more may be used mixed together. The acid used in the reaction can be introduced into the high-temperature high-pressure water using a conveying pump, either together with or separately to the reaction substrate oxime. The acid can also be used mixed into the carrier water in advance.

The concentration of the acid used can be varied in accordance with the initial temperature of the carrier water, the reaction pressure, the flow rate of the carrier water, the flow rate of introduction of the oxime aqueous solution or oxime, the amount introduced of the oxime, the form of the reactor, the volume of the reactor and so on. The acid concentration is preferably selected from a concentration range of 0.001 mM to 10 M, more preferably 0.01 mM to 5 M, yet more preferably 0.01 mM to 3 M, most preferably 0.01 mM to 1 M.

The temperature of the high-temperature high-pressure water used in the present invention can be controlled using a heater, molten salt or the like outside the reactor. Alternatively, this temperature control can be carried out using an internal heat method inside the reactor. Moreover, it is also possible to produce the high-temperature high-pressure water in advance, and inject the high-temperature high-pressure water into the reactor from the outside using a conveying pump or the like and carry out the reaction. It is also possible to feed two or more types of high-temperature high-pressure water having different temperatures and pressures to one another into the reaction system, whereby the reaction conditions can be controlled. In the case that the high-temperature high-pressure water is made to flow through the reaction vessel, the pressure inside the reaction vessel can be controlled using a pressure regulating valve. Furthermore, the pressure can also be controlled by injecting in another gas such as nitrogen gas. In general the pressure used should be at least the self-generated pressure at the temperature used.

Basically, the present invention is realized so long as the reaction is carried out in high-temperature high-pressure water at a temperature of at least 250° C. and a pressure of at least 15 MPa. The present invention can be attained more favorably if the reaction is carried out in high-temperature high-pressure water at a temperature of at least 300° C. and a pressure of at least 15 MPa. The present invention can be attained yet more favorably if the reaction is carried out in high-temperature high-pressure water at a temperature in a range of 350° C. to 420° C. and a pressure in a range of 20 MPa to 50 MPa. The present invention can be attained most favorably if the reaction is carried out in high-temperature high-pressure water at a temperature in a range of 350° C. to 400° C. and a pressure in a range of 30 MPa to 50 MPa. The ideal temperature varies according to the processing time, but in general a temperature in a range of 350° C. to 400° C. can be favorably selected. Moreover, an appropriate temperature and pressure can be adopted in accordance with the throughput and the type of the reaction apparatus. With the present invention, it has been found that the reaction tends to proceed best in a temperature range of 350° C. to 400° C. It has also been found that the reaction tends to be promoted by the pressure being higher.

As the reaction apparatus, for example a high-temperature high-pressure reaction apparatus can be used; however, there is no limitation thereto, but rather any type of apparatus can be used so long as the reaction can be carried out in high-temperature high-pressure water. Here, examples of suitable reaction apparatuses are a flow type high-temperature high-pressure reaction apparatus and a molten oxime introduction type flow type high-temperature high-pressure reaction apparatus as used in the present invention.

In the present invention, an oxime aqueous solution or an oxime at, for example, room temperature is directly introduced, possibly together with an acid, into flowing high-temperature high-pressure water or flowing high-temperature high-pressure water containing an acid, and hence the temperature of the high-temperature high-pressure water drops upon the mixing. The extent of the drop in temperature upon the mixing varies according to the initial temperature of the carrier water, the reaction pressure, the flow rate of the carrier water, the flow rate of introduction of the oxime aqueous solution or oxime, the amount introduced of the oxime, the rate of introduction of the acid, the concentration of the acid, the amount introduced of the acid, the form of the reactor, the volume of the reactor and soon. In general, from experience the set reaction temperature can be achieved by suitably selecting the initial temperature of the carrier water to be approximately 5 to 300° C. higher than the set reaction temperature.

The most distinctive feature of the present invention is that by introducing the oxime into high-temperature high-pressure water at a temperature approximately 5 to 300° C. higher than the set reaction temperature as described above, the time taken for the temperature of the oxime to rise to the set reaction temperature can be made to be a short time of not more than 3 seconds. Due to this, hydrolysis of the oxime can be suppressed, and through this and the catalytic function of the added acid, the selectivity and yield of the lactam can be dramatically improved. The time taken for the temperature of the oxime to rise to the set reaction temperature is more preferably not more than 1 second, yet more preferably not more than 0.5 seconds, most preferably not more than 0.3 seconds.

In the case of using the carrier water in a supercritical state in particular, the viscosity of the fluid is lower and the diffusion coefficient is higher than with liquid carrier water, and hence it is thought that the mixing rate is dramatically increased. Moreover, it is known that with high-temperature high-pressure water above a subcritical state close to the supercritical point, the dielectric constant is reduced and the organic matter solubility increases dramatically; it is thus thought that the solubility of oximes similarly increases, resulting in conditions suitable for the rearrangement reaction.

The reaction conditions vary according to the type and concentration of the oxime used, the volume of the reactor tube, the conditions of the high-temperature high-pressure water, and so on. In the present invention, there is no limitation to using one oxime in the reaction, but rather the reaction will still proceed favorably even if a mixture of two or more oximes is used. The oxime can be melted and introduced into the high-temperature high-pressure water and thus dissolved, or a powder of the oxime may be directly introduced into the high-temperature high-pressure water. Alternatively, a substrate aqueous solution in which the oxime has been dissolved in advance at room temperature can be introduced into the high-temperature high-pressure water.

The concentration of the oxime introduced into the reactor can be controlled by controlling the flow rate of the high-temperature high-pressure water used as the flowing carrier water and the flow rate of introduction of the reaction substrate oxime. In general, the concentration of the oxime introduced into the reactor is selected from a concentration range of 1 mM to 10 M. It is preferable to select a suitable concentration value from 2 mM to 5 M, and most preferable to select a suitable concentration value from 2 mM to 2 M, although there is no limitation to these concentration ranges in the present invention.

In the present invention, the reaction yield of the lactam can be manipulated by adjusting the temperature and pressure of the reaction system, the internal diameter of the reactor, the volume of the reactor, the flow rates, the concentration of the acid, the type of the acid, the concentration of the reaction substrate, the reaction time and so on, this being in accordance with the type of the oxime.

Regarding the reaction system in the present invention, the reaction substrate oxime and the acid need merely be made to be present in high-temperature high-pressure water at a temperature of at least 250° C. and a pressure of at least 15 MPa as described above; at this time, there is no particular need to add, for example, metal ions, a metal-supporting catalyst, a solid catalyst such as a solid acid or a solid base, an enzyme, or the like, and moreover there is also no need to use an organic solvent.

Basically, the most distinctive feature of the present invention is that a lactam is synthesized from an oxime by making a reaction substrate and an acid as described above be present in high-temperature high-pressure water, without an organic solvent being involved in the reaction; nevertheless, if necessary, it is quite acceptable to add an organic solvent such as methanol, ethanol or ethylene glycol, metal ions, a metal-supporting catalyst, a solid catalyst such as a solid acid or a solid base, or an enzyme when carrying out the reaction.

In the present invention, using the reaction system described above, a lactam is synthesized from an oxime within a short time, i.e. with a reaction time of, for example, 0.001 seconds to 60 seconds. In the case of using a flow type reaction apparatus, the reaction time can be controlled by controlling the reaction temperature, the reaction pressure, the flow rate of the high-temperature high-pressure water, the flow rate of introduction of the reaction substrate, the shape of the reactor, the internal diameter of the reactor, the length of the flow path of the reactor, and so on. The reaction time is more preferably selected from a range of 0.01 seconds to 30 seconds, is yet more preferably selected from a range of 0.05 seconds to 30 seconds, and is most preferably selected from a range of 0.05 seconds to 10 seconds, although there is no limitation to these ranges in the present invention.

As shown in the examples described later, using a high performance liquid chromatography-mass spectrometry (LC-MS) apparatus, a nuclear magnetic resonance (NMR) spectrometer and a Fourier transform infrared (FTIR) spectrophotometer, the present inventors have verified that it is possible to carry out a rearrangement reaction from an oxime to a lactam within a short time (e.g. a reaction time of approximately 1 second) in high-temperature high-pressure water. Furthermore, by using an LC-MS apparatus, the types of the oxime, the lactam, and the byproduct amino acid can be identified, and the contents thereof can be measured accurately. Moreover, by subjecting the continuously obtained lactam to separation and purification using an ion exchange resin column, measuring the infrared absorption spectrum using an FTIR spectrophotometer, and comparing with the infrared absorption spectra of high-purity special grade reagent products, the lactam can be identified accurately. Similarly, the type and purity of the lactam can also be verified by NMR spectroscopy. The structure of the lactam can be verified using a gas chromatography-mass spectrometry (GC-MS) apparatus, an LC-MS apparatus, an NMR spectrometer, and an FTIR spectrophotometer.

The reaction yield of the lactam produced in the present invention varies according to the reaction conditions such as the temperature and the pressure, the type of the acid, the concentration of the acid, the rate of introduction of the acid, the type of the oxime, the concentration of the oxime, the form of the reaction apparatus, the size of the reactor, the flow rate of the carrier water, the rate of introduction of the oxime, the reaction time, and so on. For example, in the case of ε-caprolactam, the reaction yield was from 15.9% to 98.0%. The ε-caprolactam is recovered mixed together with an amino acid and the raw material cyclohexanone oxime. Similarly, according to the present invention, any of various lactams can be recovered together with the raw material substrate(s) from any of various oximes or amino acids or a mixture thereof, but by using, for example, a cation exchange resin, an anion exchange resin, or a combination thereof, the lactam(s) and the amino acid(s) and the raw material substrate oxime(s) can be separated, and moreover a plurality of lactams can be separated from one another, and hence the lactams can be purified and concentrated type by type. The byproduct amino acid(s) can readily be converted into the lactam(s). Moreover, the oxime(s) recovered at the same time can be reused as raw material.

It is thus possible to synthesize lactam(s) by subjecting oxime(s) to a rearrangement reaction in high-temperature high-pressure water, and subject the reaction solution obtained to an ion exchange resin to separate and purify the lactam(s), whereby high-purity lactam(s) can be favorably produced.

In the present invention, a prescribed concentration of an oxime as a reaction substrate and an acid are made to be present in high-temperature high-pressure water, thus raising the temperature of the reaction substrate within a short time, and carrying out reaction in a prescribed high-temperature high-pressure aqueous state, whereby, for example, ε-caprolactam is synthesized from cyclohexanone oxime. Moreover, by continuously introducing such oximes into flowing high-temperature high-pressure water containing an acid, or continuously introducing such oximes and an acid into flowing high-temperature high-pressure water, various lactams corresponding to the respective oximes can be synthesized continuously and efficiently.

As described above, the present invention is a novel continuous lactam production method that enables any of various lactams to be produced efficiently within a short time using the reaction system described above by adjusting the reaction conditions, the type of the reaction substrate oxime, the concentration of the oxime, the type of the acid, and the concentration of the acid, and is thus useful as a lactam production method.

DESCRIPTION OF THE PREFERRED EMBODIMENTS

Following is a concrete description of the present invention through examples; however, the present invention is not limited whatsoever by the following examples.

EXAMPLE 1

Figure 1:
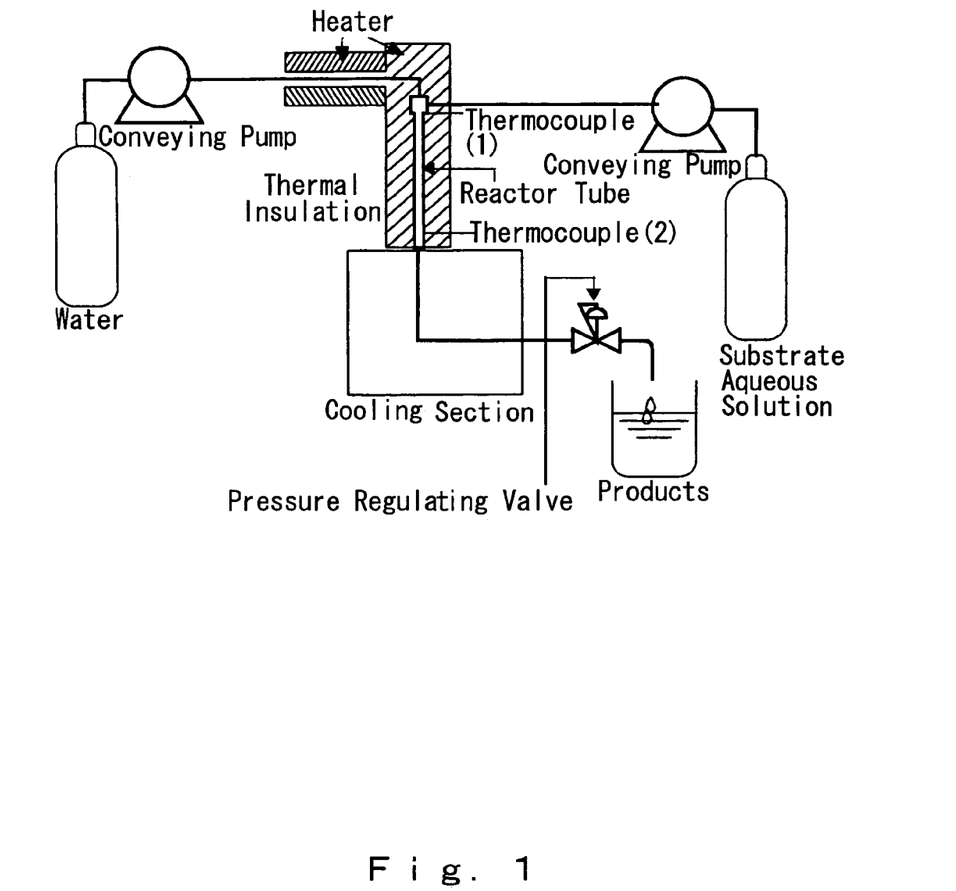
FIG. 1 shows a flow plan of a flow type high-temperature high-pressure reaction apparatus having two conveying pumps used in the present invention.

Using a continuous type high-temperature high-pressure reaction apparatus as shown in FIG. 1, continuous production of ε-caprolactam through a rearrangement reaction was attempted using a cyclohexanone oxime (purity 97%) made by Aldrich Chemical Company, Inc. and acetic acid in high-temperature high-pressure water of temperature 375° C., pressure 40 MPa and density 0.6096 g/cm$^3$.

The material of the reactor was alloy C-276, and the internal diameter of the reactor was 0.325 mm and the length of the reactor was 120 cm, and hence the volume of the reactor was calculated to be 0.0995 cm$^3$. Each of the introduced prepared liquids (i.e. the carrier water and the substrate solution) was injected in using a high-pressure pump. Distilled water from which dissolved oxygen had been driven out by bubbling with nitrogen gas was heated to produce carrier water at 480° C. and 40 MPa, and the carrier water was passed through at a flow rate of 4.0 ml/min. A substrate solution containing 22.7 mM of cyclohexanone oxime and 51.3 mM of acetic acid was prepared using similarly deoxygenated distilled water. The substrate solution was introduced at room temperature and 40 MPa into the carrier water at the reactor inlet at a flow rate of 1.0 ml/min, thus mixing the substrate solution and the carrier water together. The reaction temperature of the mixed solution measured by a thermocouple (1) installed 1 cm from the reactor inlet was 375° C., which matched the temperature measured by a thermocouple (2) at the reactor outlet, and hence it is inferred that the temperature throughout the reactor was constant, and that the carrier water and the substrate solution were mixed together homogeneously. The substrate concentration and the acetic acid concentration after the mixing were 4.54 mM and 10.26 mM respectively. The reaction time was 0.728 seconds. It is thus inferred that the mixing took place within a short time of not more than 0.006 seconds. The aqueous solution recovered after the reaction was examined using a high performance liquid chromatography-mass spectrometry apparatus, whereupon it was found that ε-caprolactam as a main product and 6-aminocaproic acid as a byproduct had been produced. The concentration of the ε-caprolactam was 4.45 mM, and hence the reaction yield thereof was 98.0%. The concentration of the 6-aminocaproic acid was 0.074 mM, and hence the reaction yield thereof was 1.6%.

In the case that an experiment was carried out under exactly the same conditions but without adding the acid, ε-caprolactam, 6-aminocaproic acid, and the raw material cyclohexanone oxime were detected. The yields of the ε-caprolactam and the 6-aminocaproic acid were 59.1% and 1.1% respectively. It is thus inferred that the rearrangement reaction of the oxime was efficiently promoted by adding the acetic acid.

EXAMPLE 2

Reaction was carried out as in Example 1, thus attempting continuous production of ε-caprolactam through a rearrangement reaction of cyclohexanone oxime. The reaction conditions, however, were changed to the following.

Reaction Conditions
Temperature and pressure of carrier water: 422° C., 30 MPa
Flow rate of carrier water: 3.9 ml/min
Temperature and pressure of substrate solution containing 22.7 mM of substrate and 8.5 mM of acetic acid: 25° C., 30 MPa
Flow rate of substrate solution: 1.1 ml/min
Temperature of high-temperature high-pressure water in the reaction: 350° C.
Pressure of high-temperature high-pressure water in the reaction: 30 MPa
Density of high-temperature high-pressure water in the reaction: 0.6443 g/cm$^3$
Flow rate of high-temperature high-pressure water in the reaction: 5.0 ml/min After the mixing, the cyclohexanone oxime substrate concentration was 4.99 mM and the acetic acid concentration was 1.9 mM. The reaction time was 0.667 seconds, and the temperature throughout the reactor was constant, and hence it is inferred that the mixing took place within a short time of not more than 0.006 seconds. The aqueous solution after the reaction was examined using a high performance liquid chromatography-mass spectrometry apparatus, whereupon it was found that ε-caprolactam as a main product and 6-aminocaproic acid as a byproduct had been produced. In addition, unreacted cyclohexanone oxime was detected. The concentration of the ε-caprolactam was 2.59 mM, and hence the reaction yield thereof was 51.9%. The concentration of the 6-aminocaproic acid was 0.010 mM, and hence the reaction yield thereof was 0.2%.

In the case that an experiment was carried out under exactly the same conditions but without adding the acid, ε-caprolactam, 6-aminocaproic acid, and the raw material cyclohexanone oxime were detected. The yields of the ε-caprolactam and the 6-aminocaproic acid were 33.4% and 0.2% respectively. It is thus inferred that the rearrangement reaction of the oxime was promoted by adding the acetic acid.

EXAMPLE 3

Reaction was carried out as in Example 1, thus attempting continuous production of ε-caprolactam through a rearrangement reaction of cyclohexanone oxime. The reaction conditions, however, were changed to the following.

Reaction Conditions
Temperature and pressure of carrier water: 348° C., 15 MPa
Flow rate of carrier water: 3.1 ml/min
Temperature and pressure of substrate solution containing 22.7 mM of substrate and 0.5385 M of acetic acid: 25° C., 15 MPa
Flow rate of substrate solution: 2.0 ml/min
Temperature of high-temperature high-pressure water in the reaction: 300° C.
Pressure of high-temperature high-pressure water in the reaction: 15 MPa
Density of high-temperature high-pressure water in the reaction: 0.7259 g/cm$^3$
Flow rate of high-temperature high-pressure water in the reaction: 5.1 ml/min After the mixing, the cyclohexanone oxime substrate concentration was 9.02 mM and the acetic acid concentration was 0.2112 M. The reaction time was 0.867 seconds, and the temperature throughout the reactor was constant, and hence it is inferred that the mixing together of the carrier water and the substrate solution took place within a short time of not more than 0.007 seconds. The aqueous solution after the reaction was examined using a high performance liquid chromatography-mass spectrometry apparatus, whereupon it was found that ε-caprolactam had been produced as a product. In addition, unreacted cyclohexanone oxime was detected. The concentration of the ε-caprolactam was 2.40 mM, and hence the reaction yield thereof was 26.6%.

In the case that an experiment was carried out under exactly the same conditions but without adding the acid, ε-caprolactam and the raw material cyclohexanone oxime were detected. The yield of the ε-caprolactam was 5.5%. It is thus inferred that the rearrangement reaction of the oxime was promoted by adding the acetic acid.

EXAMPLE 4

Reaction was carried out as in Example 1, thus attempting continuous production of ε-caprolactam through a rearrangement reaction of cyclohexanone oxime. The reaction conditions, however, were changed to the following.

Reaction Conditions
Temperature and pressure of carrier water: 345° C., 15 MPa
Flow rate of carrier water: 3.0 ml/min
Temperature and pressure of substrate solution containing 22.7 mM of substrate and 0.5385 M of acetic acid: 25° C., 15 MPa
Flow rate of substrate solution: 2.0 ml/min
Temperature of high-temperature high-pressure water in the reaction: 250° C.
Pressure of high-temperature high-pressure water in the reaction: 15 MPa
Density of high-temperature high-pressure water in the reaction: 0.8112 g/cm$^3$
Flow rate of high-temperature high-pressure water in the reaction: 5.0 ml/min After the mixing, the cyclohexanone oxime substrate concentration was 9.08 mM and the acetic acid concentration was 0.2154 M. The reaction time was 0.969 seconds, and the temperature throughout the reactor was constant, and hence it is inferred that the mixing together of the carrier water and the substrate solution took place within a short time of not more than 0.008 seconds. The aqueous solution after the reaction was examined using a high performance liquid chromatography-mass spectrometry apparatus, whereupon it was found that ε-caprolactam had been produced as a product. In addition, unreacted cyclohexanone oxime was detected. The concentration of the ε-caprolactam was 1.44 mM, and hence the reaction yield thereof was 15.9%.

In the case that an experiment was carried out under exactly the same conditions but without adding the acid, ε-caprolactam and the raw material cyclohexanone oxime were detected. The yield of the ε-caprolactam was 0.6%. It is thus inferred that the rearrangement reaction of the oxime was promoted by adding the acetic acid.

COMPARATIVE EXAMPLE 1

Reaction was carried out as in Example 1, thus attempting continuous production of ε-caprolactam through a rearrangement reaction of cyclohexanone oxime. The reaction conditions, however, were changed to the following.

Reaction Conditions
Temperature and pressure of carrier water: 314° C., 15 MPa
Flow rate of carrier water: 3.5 ml/min
Temperature and pressure of substrate solution containing 22.7 mM of substrate and 0.5385 M of acetic acid: 25° C., 15 MPa
Flow rate of substrate solution: 1.5 ml/min
Temperature of high-temperature high-pressure water in the reaction: 200° C.
Pressure of high-temperature high-pressure water in the reaction: 15 MPa
Density of high-temperature high-pressure water in the reaction: 0.8746 g/cm$^3$
Flow rate of high-temperature high-pressure water in the reaction: 5.0 ml/min After the mixing, the cyclohexanone oxime substrate concentration was 6.81 mM and the acetic acid concentration was 0.1616 M. The reaction time was 1.066 seconds, and the temperature throughout the reactor was constant, and hence it is inferred that the mixing together of the carrier water and the substrate solution took place within a short time of not more than 0.009 seconds. The aqueous solution after the reaction was examined using a high performance liquid chromatography-mass spectrometry apparatus, whereupon production of ε-caprolactam was not detected at all.

In the case that an experiment was carried out under exactly the same conditions but without adding the acid, again production of ε-caprolactam was not detected at all.

COMPARATIVE EXAMPLE 2

Reaction was carried out as in Example 1, thus attempting continuous production of ε-caprolactam through a rearrangement reaction of cyclohexanone oxime. The reaction conditions, however, were changed to the following.

Reaction Conditions
Temperature and pressure of carrier water: 345° C., 9 MPa
Flow rate of carrier water: 3.3 ml/min
Temperature and pressure of substrate solution containing 22.7 mM of substrate and 0.5385 M of acetic acid: 25° C., 9 MPa
Flow rate of substrate solution: 1.7 ml/min
Temperature of high-temperature high-pressure water in the reaction: 300° C.
Pressure of high-temperature high-pressure water in the reaction: 9 MPa
Density of high-temperature high-pressure water in the reaction: 0.7134 g/cm$^3$
Flow rate of high-temperature high-pressure water in the reaction: 5.0 ml/min After the mixing, the cyclohexanone oxime substrate concentration was 7.72 mM and the acetic acid concentration was 0.1831 M. The reaction time was 0.852 seconds, and the temperature throughout the reactor was constant, and hence it is inferred that the mixing together of the carrier water and the substrate solution took place within a short time of not more than 0.007 seconds. The aqueous solution after the reaction was examined using a high performance liquid chromatography-mass spectrometry apparatus, whereupon production of ε-caprolactam was not detected at all.

In the case that an experiment was carried out under exactly the same conditions but without adding the acid, again production of ε-caprolactam was not detected at all.

EXAMPLE 5

Reaction was carried out as in Example 1, thus attempting continuous production of ε-caprolactam through a rearrangement reaction of cyclohexanone oxime. However, nitric acid was used and the reaction conditions were changed to the following.

Reaction Conditions
Temperature and pressure of carrier water: 500° C., 40 MPa
Flow rate of carrier water: 3.8 ml/min
Temperature and pressure of substrate solution containing 22.1 mM of substrate and 1.6 mM of nitric acid: 25° C., 40 MPa
Flow rate of substrate solution: 1.2 ml/min
Temperature of high-temperature high-pressure water in the reaction: 380° C.
Pressure of high-temperature high-pressure water: in the reaction 40 MPa
Density of high-temperature high-pressure water in the reaction: 0.5948 g/cm$^3$
Flow rate of high-temperature high-pressure water in the reaction: 5.0 ml/min After the mixing, the cyclohexanone oxime substrate concentration was 5.30 mM and the nitric acid concentration was 0.38 mM. The reaction time was 0.710 seconds, and the temperature throughout the reactor was constant, and hence it is inferred that the mixing took place within a short time of not more than 0.006 seconds. The aqueous solution after the reaction was examined using a high performance liquid chromatography-mass spectrometry apparatus, whereupon it was found that ε-caprolactam as a main product and 6-aminocaproic acid as a byproduct had been produced. The concentration of the ε-caprolactam was 5.14 mM, and hence the reaction yield thereof was 97.0%. The concentration of the 6-aminocaproic acid was 0.15 mM, and hence the reaction yield thereof was 2.8%.

EXAMPLE 6

Reaction was carried out as in Example 1, thus attempting continuous production of ε-caprolactam through a rearrangement reaction of cyclohexanone oxime. However, hydrochloric acid was used and the reaction conditions were changed to the following.

Reaction Conditions
Temperature and pressure of carrier water: 500° C., 40 MPa
Flow rate of carrier water: 3.7 ml/min
Temperature and pressure of substrate solution containing 22.1 mM of substrate and 0.30 mM of hydrochloric acid: 25° C., 40 MPa
Flow rate of substrate solution: 1.3 ml/min
Temperature of high-temperature high-pressure water in the reaction: 375° C.
Pressure of high-temperature high-pressure water in the reaction: 40 MPa
Density of high-temperature high-pressure water in the reaction: 0.6096 g/cm$^3$
Flow rate of high-temperature high-pressure water in the reaction: 5.0 ml/min After the mixing, the cyclohexanone oxime substrate concentration was 5.75 mM and the hydrochloric acid concentration was 0.078 mM. The reaction time was 0.728 seconds, and the temperature throughout the reactor was constant, and hence it is inferred that the mixing took place within a short time of not more than 0.006 seconds. The aqueous solution after the reaction was examined using a high performance liquid chromatography-mass spectrometry apparatus, whereupon it was found that ε-caprolactam as a main product and 6-aminocaproic acid as a byproduct had been produced. The concentration of the ε-caprolactam was 5.53 mM, and hence the reaction yield thereof was 96.2%. The concentration of the 6-aminocaproic acid was 0.20 mM, and hence the reaction yield thereof was 3.5%.

EXAMPLE 7

Reaction was carried out as in Example 1, thus attempting continuous production of ε-caprolactam through a rearrangement reaction of cyclohexanone oxime. However, sulfuric acid was used and the reaction conditions were changed to the following.

Reaction Conditions
Temperature and pressure of carrier water: 550° C., 40 MPa
Flow rate of carrier water: 3.8 ml/min
Temperature and pressure of substrate solution containing 22.1 mM of substrate and 0.5 mM of sulfuric acid: 25° C., 40 MPa
Flow rate of substrate solution: 1.2 ml/min
Temperature of high-temperature high-pressure water in the reaction: 380° C.
Pressure of high-temperature high-pressure water in the reaction: 40 MPa
Density of high-temperature high-pressure water in the reaction: 0.5948 g/cm$^3$
Flow rate of high-temperature high-pressure water in the reaction: 5.0 ml/min After the mixing, the cyclohexanone oxime substrate concentration was 5.30 mM and the sulfuric acid concentration was 0.12 mM. The reaction time was 0.710 seconds, and the temperature throughout the reactor was constant, and hence it is inferred that the mixing took place within a short time of not more than 0.006 seconds. The aqueous solution after the reaction was examined using a high performance liquid chromatography-mass spectrometry apparatus, whereupon it was found that ε-caprolactam as a main product and 6-aminocaproic acid as a byproduct had been produced. In addition, a small amount of unreacted cyclohexanone oxime was detected. The concentration of the ε-caprolactam was 4.94 mM, and hence the reaction yield thereof was 93.2%. The concentration of the 6-aminocaproic acid was 0.14 mM, and hence the reaction yield thereof was 2.6%.

EXAMPLE 8

Reaction was carried out as in Example 1, thus attempting continuous production of ε-caprolactam through a rearrangement reaction of cyclohexanone oxime. However, sulfuric acid was used and the reaction conditions were changed to the following.

Reaction Conditions
Temperature and pressure of carrier water: 475° C., 40 MPa
Flow rate of carrier water: 15.6 ml/min
Temperature and pressure of substrate solution containing 22.1 mM of substrate and 5 mM of sulfuric acid: 25° C., 40 MPa
Flow rate of substrate solution: 4.4 ml/min
Temperature of high-temperature high-pressure water in the reaction: 375° C.
Pressure of high-temperature high-pressure water in the reaction: 40 MPa
Density of high-temperature high-pressure water: in the reaction 0.6096 g/cm$^3$
Flow rate of high-temperature high-pressure water in the reaction: 20.0 ml/min After the mixing, the cyclohexanone oxime substrate concentration was 4.86 mM. The reaction time was 0.182 seconds, and the temperature throughout the reactor was constant, and hence it is inferred that the mixing took place within a short time of not more than 0.002seconds. The aqueous solution after the reaction was examined using a high performance liquid chromatography-mass spectrometry apparatus, whereupon it was found that ε-caprolactam as a main product and 6-aminocaproic acid as a byproduct had been produced. The concentration of the ε-caprolactam was 4.53 mM, and hence the reaction yield thereof was 93.2%. The concentration of the 6-aminocaproic acid was 0.26 mM, and hence the reaction yield thereof was 5.3%.

EXAMPLE 9

Figure 2:
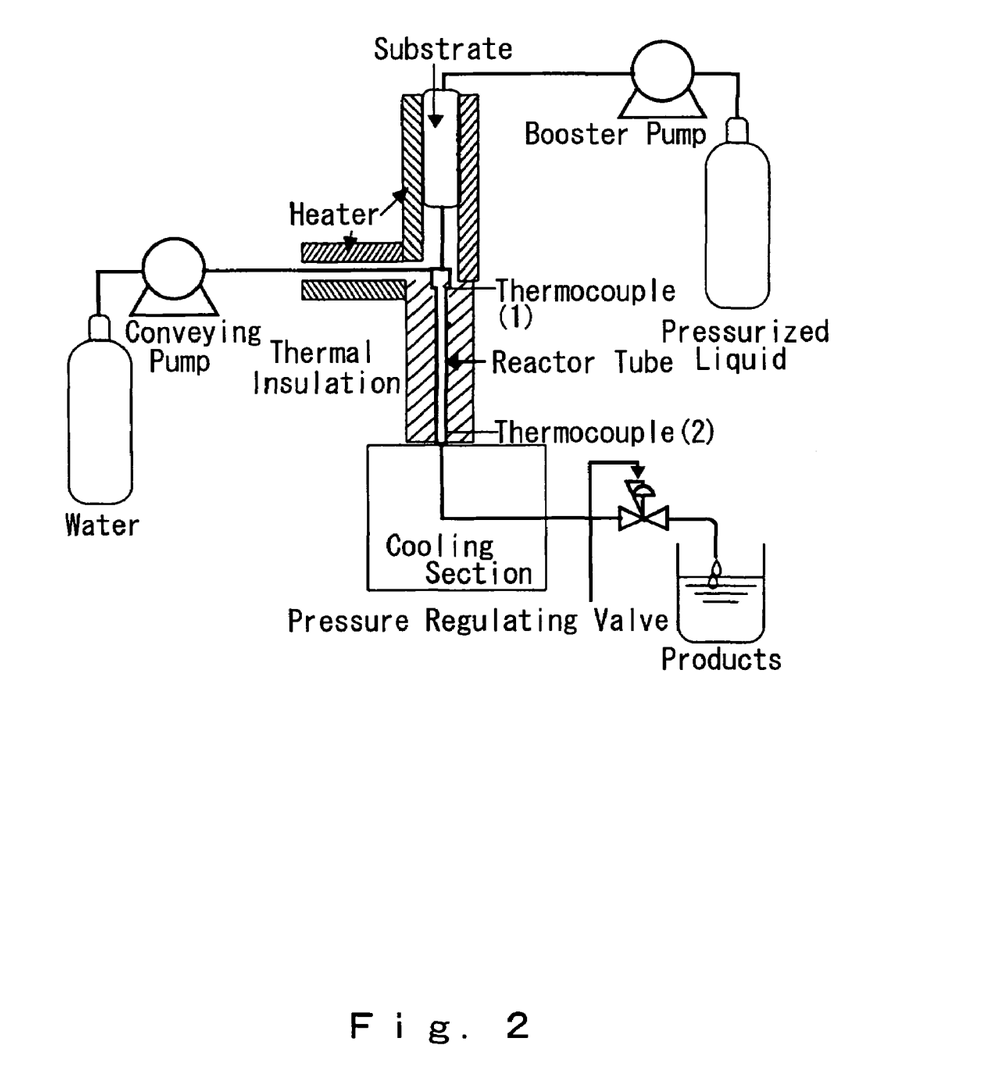
FIG. 2 shows a flow plan of a molten oxime introduction type flow type high-temperature high-pressure reaction apparatus having two conveying pumps used in the present invention.

Using a continuous type reaction apparatus as shown in FIG. 2, continuous production of ε-caprolactam through a rearrangement reaction was attempted by introducing a melt of cyclohexanone oxime (purity 97%) made by Aldrich Chemical Company, Inc. into high-temperature high-pressure water of temperature 350° C., pressure 30 MPa and density 0.6443 g/cm$^3$.

The material of the reactor was alloy C-276, and the internal diameter of the reactor was 4.68 mm and the length of the reactor was 200 mm, and hence the volume of the reactor was calculated to be 3.440 cm$^3$. Each of the introduced prepared liquids (i.e. the carrier water and the substrate melt) was injected in using a high-pressure pump. Sulfuric acid was added to distilled water to make the sulfuric acid concentration 0.02 M, dissolved oxygen was driven out by bubbling with nitrogen gas, and then heating was carried out to produce carrier water at 357° C. and 30 MPa, and the carrier water was passed through at a flow rate of 24.6 ml/min. The cyclohexanone oxime was heated on 95° C. to prepare the substrate melt. The substrate melt was pressurized to 30 MPa using pressurized water and introduced into and thus mixed with the carrier water at the reactor inlet at a flow rate of 0.4 ml/min. The reaction temperature of the mixed solution measured by a thermocouple (1) installed 1 cm from the reactor inlet was 350° C., which matched the temperature measured by a thermocouple (2) at the reactor outlet, and hence it is inferred that the temperature throughout the reactor was constant, and that the substrate melt and the carrier water containing the sulfuric acid were mixed together homogeneously. The substrate concentration after the mixing was 141.6 mM and the sulfuric acid concentration was 19.7 mM. The reaction time was 5.165 seconds. It is thus inferred that the mixing and dissolution was completed within a short time of not more than 0.258 seconds. The aqueous solution after the reaction was examined using a high performance liquid chromatography-mass spectrometry apparatus, whereupon it was found that $\epsilon$-caprolactam as a main product and 6-aminocaproic acid as a byproduct had been produced. The concentration of the $\epsilon$-caprolactam was 129.8 mM, and hence the reaction yield thereof was 91.7%. The concentration of the 6-aminocaproic acid was 10.3 mM, and hence the reaction yield thereof was 7.3%.

EXAMPLE 10

Reaction was carried out as in Example 1, thus attempting continuous production of $\epsilon$-caprolactam through a rearrangement reaction of cyclohexanone oxime. However, carrier water having nitric acid dissolved therein was used, and the reaction conditions were changed to the following.

Reaction Conditions
Concentration of nitric acid in carrier water: 0.8 mM
Temperature and pressure of carrier water: 500° C., 40 MPa
Flow rate of carrier water: 3.8 ml/min
Temperature and pressure of substrate solution containing 22.1 mM of substrate: 25° C., 40 MPa
Flow rate of substrate solution: 1.2 ml/min
Temperature of high-temperature high-pressure water in the reaction: 380° C.
Pressure of high-temperature high-pressure water in the reaction: 40 MPa
Density of high-temperature high-pressure water in the reaction: 0.5948 g/cm$^3$
Flow rate of high-temperature high-pressure water in the reaction: 5.0 ml/min After the mixing, the cyclohexanone oxime substrate concentration was 5.30 mM and the nitric acid concentration was 0.61 mM. The reaction time was 0.710 seconds, and the temperature throughout the reactor was constant, and hence it is inferred that the mixing took place within a short time of not more than 0.006 seconds. The aqueous solution after the reaction was examined using a high performance liquid chromatography-mass spectrometry apparatus, whereupon it was found that $\epsilon$-caprolactam as a main product and 6-aminocaproic acid as a byproduct had been produced. The concentration of the $\epsilon$-caprolactam was 5.16 mM, and hence the reaction yield thereof was 97.4%. The concentration of the 6-aminocaproic acid was 0.13 mM, and hence the reaction yield thereof was 2.5%.

EXAMPLE 11

Figure 3:
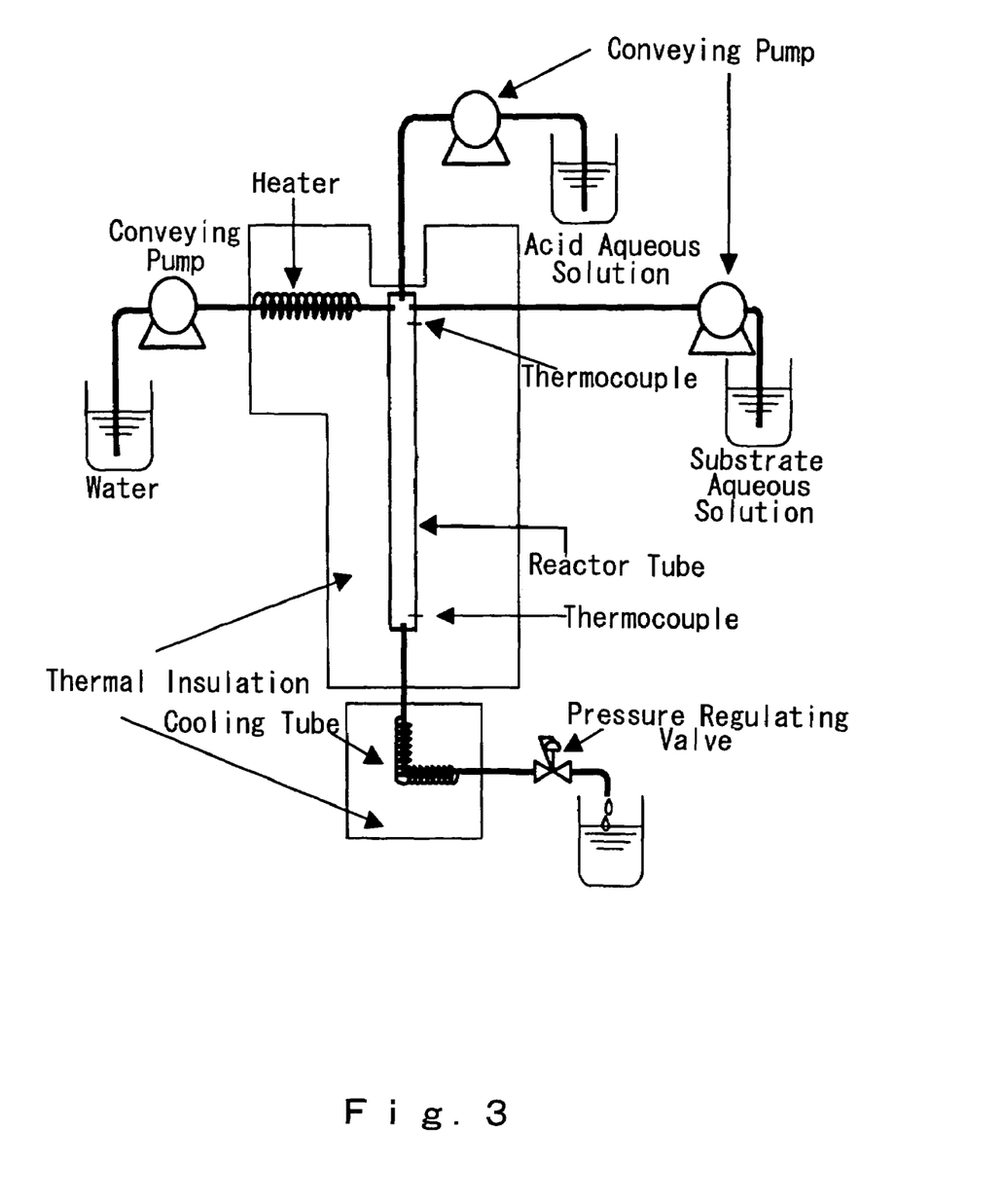
FIG. 3 shows a flow plan of a flow type high-temperature high-pressure reaction apparatus having three conveying pumps used in the present invention.

Reaction was carried out as in Example 1, thus attempting continuous production of $\epsilon$-caprolactam through a rearrangement reaction of cyclohexanone oxime. However, a 3.2 mM nitric acid aqueous solution was prepared from distilled water from which dissolved oxygen had been removed, a continuous reaction apparatus as shown in FIG. 3 was used, and the nitric acid aqueous solution and the substrate aqueous solution were injected into the reactor using two different conveying pumps, and moreover the reaction conditions were changed to the following.

Reaction Conditions
Temperature and pressure of carrier water: 500° C., 40 MPa
Flow rate of carrier water: 3.8 ml/min
Temperature and pressure of substrate solution containing 22.1 mM of substrate: 25° C., 40 MPa
Flow rate of substrate solution: 0.6 ml/min
Temperature and pressure of 3.2 mM nitric acid aqueous solution: 25° C., 40 MPa
Flow rate of nitric acid aqueous solution: 0.6 ml/min
Temperature of high-temperature high-pressure water in the reaction 380° C.
Pressure of high-temperature high-pressure water in the reaction: 40 MPa
Density of high-temperature high-pressure water in the reaction: 0.5948 g/cm$^3$
Flow rate of high-temperature high-pressure water in the reaction: 5.0 ml/min After the mixing, the cyclohexanone oxime substrate concentration was 2.65 mM and the nitric acid concentration was 0.48 mM. The reaction time was 0.710 seconds, and the temperature throughout the reactor was constant, and hence it is inferred that the mixing took place within a short time of not more than 0.006 seconds. The aqueous solution after the reaction was examined using a high performance liquid chromatography-mass spectrometry apparatus, whereupon it was found that $\epsilon$-caprolactam as a main product and 6-aminocaproic acid as a byproduct had been produced. The concentration of the $\epsilon$-caprolactam was 2.57 mM, and hence the reaction yield thereof was 97.0%. The concentration of the 6-aminocaproic acid was 0.07 mM, and hence the reaction yield thereof was 2.6%.

INDUSTRIAL APPLICABILITY

As described in detail above, the present invention relates to a continuous lactam production method in which a lactam is continuously synthesized while suppressing oxime hydrolysis by introducing an oxime as a reaction substrate and an acid into a reaction zone through which high-temperature high-pressure water is flowing, whereby reaction is carried out with the reaction substrate being put into a prescribed high-temperature high-pressure state within a short time, this being a continuous lactam production method in which a lactam is produced selectively from an oxime in high-temperature high-pressure water using an acid. According to the present invention, the following remarkable effects are attained: 1) a lactam can be produced selectively from an oxime by suppressing hydrolysis of the oxime in high-temperature high-pressure water; 2) a lactam can be produced within a short time by reacting an oxime under high temperature and high pressure; 3) a method of producing a lactam efficiently using an acid as a catalyst can be provided; and 4) the chemical substance production system is environmentally friendly.

What is claimed is:

1. A method for continuously producing caprolactam, comprising
introducing an oxime as a reaction substrate, and at least one acid into continuously flowing high-temperature high-pressure water,
raising the temperature of the oxime to put the oxime into a prescribed high-temperature high-pressure state within a short time, and subjecting the oxime to a rearrangement reaction to synthesize the lactam; wherein the temperature of the high-temperature high-pressure state is at least 375° C.;

wherein the pressure of the high-temperature high-pressure state is at least 40 MPa;

wherein the raising the temperature of the oxime occurs in less than or equal to 0.3 seconds;

wherein the oxime has the formula (1)

wherein n is 3 and $R_1$ is hydrogen or an alkyl group; and wherein the at least one acid is selected from the group consisting of sulfuric acid, hydrochloric acid, nitric acid and acetic acid.

2. The method of claim 1, wherein a substrate aqueous solution having the oxime and the acid dissolved therein is introduced into the continuously flowing high-temperature high-pressure water, thus subjecting the oxime to the reaction in the prescribed high-temperature high-pressure state.

3. The method of claim 1, wherein the oxime and the acid are introduced separately into the continuously flowing high-temperature high-pressure water, thus subjecting the oxime to the reaction in the prescribed high-temperature high-pressure state.

4. The method of producing caprolactam according to any one of claims 1 through 3, wherein the oxime is introduced in a molten state, thus subjecting the oxime to the reaction in the prescribed high-temperature high-pressure state.

5. The method of producing caprolactam according to any one of claims 1 through 3, wherein the oxime is subjected to the reaction in the prescribed high-temperature high-pressure state for a time in a range of 0.001 seconds to 60 seconds.

6. The method of producing caprolactam according to any one of claims 1 through 3, wherein the concentration of the at least one acid in the reaction is from 0.001 mM to 10 M.

7. The method of producing caprolactam according to claim 4, wherein the oxime is subjected to the reaction in the prescribed high-temperature high-pressure state for a time in a range of 0.001 seconds to 60 seconds.

8. The method of producing caprolactam according to claim 4, wherein the concentration of the at least one acid in the reaction is from 0.00 1 mM to 10 M.

9. The method of producing caprolactam according to claim 5, wherein the concentration of the at least one acid in the reaction is from 0.001 mM to 10 M.

10. The method of claim 1, wherein $R_1$ is hydrogen.

11. The method of claim 1, wherein $R_1$ is an alkyl group.

12. The method of claim 11, wherein the alkyl group comprises from 1 to 20 carbon atoms.

13. The method of claim 12, wherein the alkyl group is selected from the group consisting of methyl, ethyl, propyl and butyl.

* * * * *